United States Patent
Taylor et al.

(10) Patent No.: US 7,650,782 B2
(45) Date of Patent: Jan. 26, 2010

(54) DEVICE FOR USE IN RATING ENGINE DEPOSITS

(75) Inventors: Patrick J. Taylor, Rancho Cordova, CA (US); Paul T. Vela, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 124 days.

(21) Appl. No.: 12/022,753

(22) Filed: Jan. 30, 2008

(65) Prior Publication Data

US 2009/0139319 A1    Jun. 4, 2009

Related U.S. Application Data

(60) Provisional application No. 60/991,318, filed on Nov. 30, 2007.

(51) Int. Cl.
*G01M 15/02* (2006.01)
(52) U.S. Cl. .................................................. 73/114.77
(58) Field of Classification Search ............. 73/114.02, 73/114.55, 114.56, 114.77, 114.78, 114.79
See application file for complete search history.

(56) References Cited

U.S. PATENT DOCUMENTS

| | | | | |
|---|---|---|---|---|
| 4,869,224 A | * | 9/1989 | Ishikawa et al. | 123/682 |
| 5,118,194 A | | 6/1992 | Mather et al. | |
| 5,492,005 A | * | 2/1996 | Homan et al. | 73/61.62 |
| 5,693,874 A | * | 12/1997 | De La Cruz et al. | 73/61.62 |
| 6,370,946 B1 | * | 4/2002 | Lacey et al. | 73/61.62 |
| 2003/0192369 A1 | * | 10/2003 | Brazeau et al. | 73/118.1 |
| 2004/0149009 A1 | * | 8/2004 | Brazeau et al. | 73/23.31 |

OTHER PUBLICATIONS

"Engine Evaluation of Automotive Oil Service Properties" by Grigorev et. Al., , Khimiya I Tekhnologiya Topliv I Masel. No. 6. pp. 8-52. Jun. 1966.

* cited by examiner

*Primary Examiner*—Eric S McCall
(74) *Attorney, Agent, or Firm*—Penny Prater

(57) ABSTRACT

A sectioning device for use in dividing an engine part into sections for rating is provided. The sectioning device has a plurality of sectioners that are slidingly engaged in grooves of two separate plates, held together by at least a fastener. In operation, the sectioners can be adjusted to accommodate engine parts of different sizes, with minimal damages and losses of engine deposits in the rating process.

19 Claims, 1 Drawing Sheet

DEVICE FOR USE IN RATING ENGINE DEPOSITS

CROSS REFERENCE TO RELATED APPLICATIONS

This application claims priority to U.S. Patent Application Ser. No. 60/991,318, filed Nov. 28, 2007, the disclosure of which is incorporated herein by reference.

TECHNICAL FIELD

The invention relates generally to a device for use to rate deposits on engine parts. In one embodiment, the invention relates to a device for use in rating deposits on engine pistons.

BACKGROUND

Internal combustion engines, in the process of operation, experience engine wear and fouling with engine deposits overtime. As the engine continues in operation and with the use of hydrocarbon fuels, there is a build up of thermal oxide derived varnish like/lacquer deposits on the surfaces of the combustion chamber and components. The piston is typically the most highly stressed part of the engine, getting deposits on the surface and in the grooves, resulting in piston ring sticking, piston scuffing, and ring and cylinder wear. There are various industry and manufacturers standards and methods governing the deposit formation of automotive engine oils and the classification and quantification of lacquer and carbon deposits, e.g., to rate an engine oil, a test piston which has been subjected to many hours of operation in a running engine is rated. The Coordinating Research Counsel (CRC) has developed a standard rating scale for lacquer and carbon deposits on engine parts. Lubricant efficacy can be measured, in part, by classifying and measuring the amount of lacquer and carbon deposited on its surface and in the ring grooves in terms of color, thickness, hardness, etc. In one rating method, deposits are evaluated by volume and appearance, ranging from 10 (clean absence of deposits) to 0 (maximum deposits).

Various instruments and devices have been proposed to carry out the piston deposit rating job. U.S. Pat. No. 5,118,194 discloses an optical inspection system with sensors, a video imaging system and means to process the digital presentation of the deposits. However, rating is not as easy as matching the closest shade of color. There are different parts to rate, e.g., pistons, gears, oil pans, etc.) as well as different types of engines. Rating is ideally done in a laboratory setting under controlled conditions of light and temperature to ensure uniformity. However, this is not always the case there are needs to field rating of equipment parts in remote locations, e.g., a mine, an ocean freighter, etc.

As optoelectronic solutions are not yet fully developed and practical, deposit rating is still most reliably done by human raters. Most raters follow a breakdown examination method in which the part, e.g., a piston, is broken down or divided into sections for careful examination of each individual section.

The invention relates to a device for use in rating engine deposits, allowing engine raters to divide an engine part, e.g., a piston, into sections for examination/rating with minimal disruption to the fragile deposits on the part. The device also allows raters to rate pistons of various sizes/types, e.g., from small pistons for use in weed whackers to large-sized pistons for use in locomotives, with the use of an adjustable rating device.

SUMMARY OF THE INVENTION

In one aspect, the invention relates to a rating device for dividing an engine part into sections for deposit rating, the device comprising: a first plate having a first opening; a second plate having a second opening which aligns with the first opening; a plurality of grooves disposed on either the first plate or the second plate; a plurality of extension members, each extension member having at least a bend forming an extensioner with a downward bend; a fastener for fastening the top plate and the bottom plate through the aligned openings and securing the sectioners in-between the plates. In one embodiment, the bend is at a 90 degree angle with the downward bend being perpendicular to the first plate and the second plate. In deposit rating operation, the fastener is disengaged for the sectioners to be slidingly engaged in the grooves and the downward bends to be in engaging contact with the engine part, defining separate sections on the engine part.

In another aspect, the invention relates to a method to rate engine parts using a sectioning device with adjustable sectioners which are slidingly engaged in grooves formed between two separate plates.

DETAILED DESCRIPTION

The reference to "piston" (or pistons) in the subsequent sections is by way of exemplification only, and is not intended to exclude other engine parts in combustion engines wherein carbon deposits are formed.

As used herein, the term "sectioning device" may be used interchangeably with "rating device," referring to the device (or apparatus) described herein for use in sectioning engine parts for deposits rating. Engine deposits can be varnish, sludge, thermal oxidative oil, oleaginous liquid deposits, etc., from engine oil deposits or other sources. Deposits can be evaluated according to various factors, including volume (thickness), appearance, color, etc., wherein the engine part is first divided into sections via the use of the sectioning device so that the sections can be observed, measured, and tracked.

Figure 1:
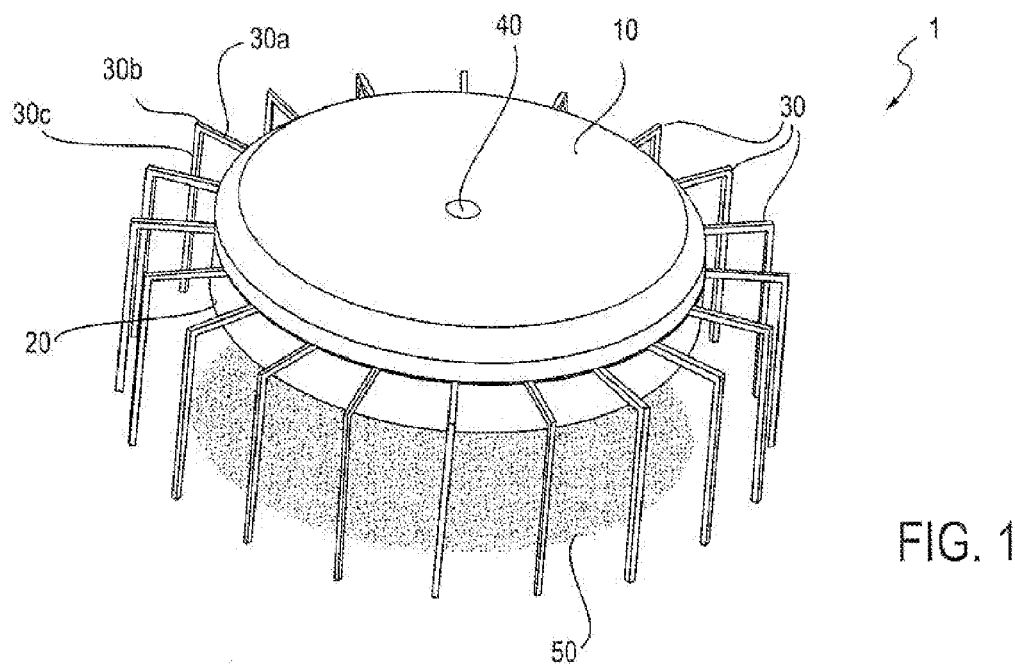
FIG. 1 is a perspective view of an embodiment of a rating device.

Sectioning Device:

In one embodiment of the invention as shown in FIG. 1, a sectioning device 1 is provided with a first (top) plate 10, a second (bottom) plate 20, a plurality of extension members 30, a fastener 40 for holding the sectioning device assembly 1 together. The extension members 30 are slidably engaged with either or both the first top plate 10 and the second bottom plate 20. Each extension member 30 has at least a bend 30b varying over a wide angle range (e.g., from 15 to 165°) to accommodate the geometry and size of the engine part 50 (e.g., a piston) to be rated, with the extension sectioner 30a being partially held in-between the top and bottom plates in assembly. Depending on the construction material for the extension member 30a, the bend 30b can be permanent (rigid extension member 30) or temporary (bendable extension member that can be bent again and again at different angles each time).

In operation and in one embodiment with a 90° bend, the downward bends 30b extend downwards forming section dividers 30c that are perpendicular to the plates 10 and 20, separating the grooves and land surface of the engine part into separate sections. In assembly, depending on the number of section members 30 used in a rating process, the sections defined by the section dividers 30c may be equal or of different sizes (width) as desired by the device operator. In one embodiment (as shown), the extension members 30 define equal sections on an engine part rated for deposit formation.

Figure 2:
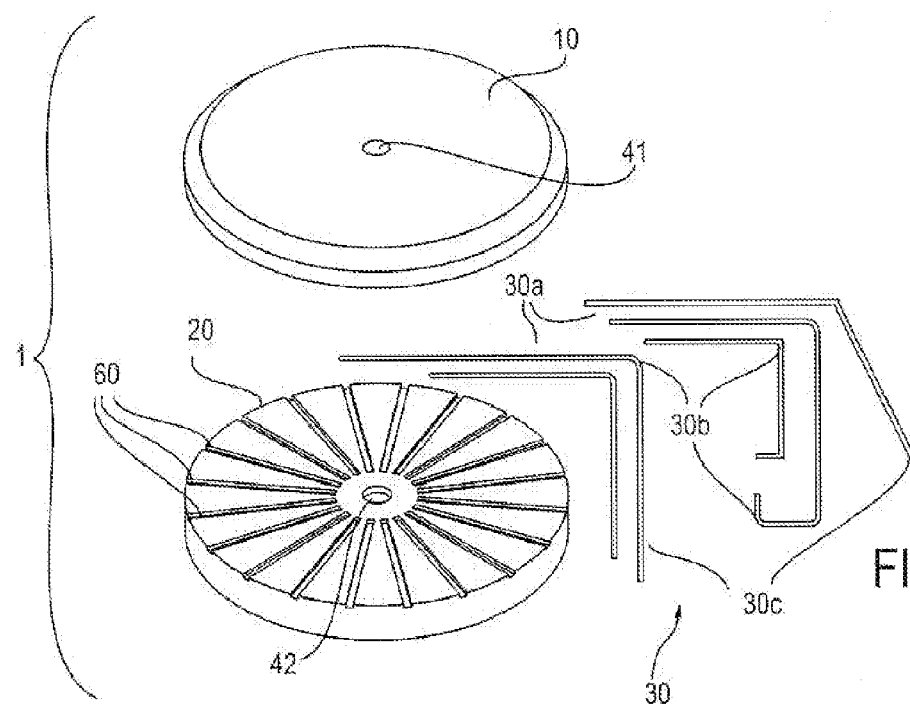
FIG. 2 is an exploded perspective view of an embodiment of the rating device of FIG. 1.

FIG. 2 is an exploded view of an embodiment of the components of the section device of FIG. 1. The construction of the section device in one embodiment is held by a single central fastener (not shown in FIG. 2) so that the device can be easily and quickly assembled or disassembled.

In one embodiment, the fastener is of a type known in the art for fastening plates together, e.g., a pin or a dowel. In another embodiment, the fastener is an assembly of a nut body and an externally threaded cylindrical core bolt (shank) in threaded engagement with the nut body, extending downwardly through the openings (bores or holes) 41 and 42 of the top plate and the bottom plate respectively.

In one embodiment (not shown), a gasket (compression material) is provided in between the top plate 10 and the bottom plate 20 to keep the extension sectioners 30a firmly in place while allowing for some variance (tolerance).

In one embodiment (not shown), instead of or in addition to the central openings 41 and 42 in the top and bottom plates, both plates have a plurality of openings located equidistance (or at random) on the plates. The plurality of openings are for use with mating fasteners in rating operations to rigidly secure the top plate 10, the bottom plate 20, and the extension members in-between the plates.

In one embodiment (not shown) with the top and bottom plates being solid (without any openings or holes), the fastener 40 is in the form of a clamp for clamping the top and bottom plates together at the edges of the plates. There can be multiple clamps for fastening the top and the bottom plates at various locations around the plates.

The fastener's function (or fasteners) is to clamp the plates, an optional gasket, and the extension members tightly in place. In one embodiment as illustrated, the bottom plate 20 has a plurality of machined grooves 60 disposed equidistantly and radially from the circumference of the top surface of the bottom plate 20. The grooves 60 house and allow the extension sectioners 30a to slide in and out along the length of the grooves in a spoke pattern. As the extension sectioners slide along the grooves 60, their length is adjusted or extended to accommodate pistons of different sizes. Although not shown, each groove 60 can be optionally numbered (engraved on the plate) so that piston sections can be easily tracked in rating studies. In one embodiment, the grooves are in the form of recesses machined into the surface of the plate. In another embodiment, the grooves are in the form of raised channels.

In one embodiment (not shown) instead of or in addition to the grooves 60 on the bottom plate 20, the top plate 10 contains a plurality of machine grooves disposed radially on its bottom surface facing the extension members 30, allowing the extension sectioners 30a to slide in and out of the grooves to accommodate engine parts of varying geometries and sizes.

In the embodiment as shown in the figures, there are 20 grooves on the plate. The number of grooves (and corresponding extension members) can be varied depending on the number of breakdown sections desired on the engine part, thus allowing for careful examination of each individual section. There can be more grooves than desired sections, for example, the device may have 40 grooves (and 40 corresponding extension members). If a device operator needs only 20 breakdown sections, the device operator inspector will use only 20 extension members/grooves for 20 breakdown sections. The device operator may way to use extension members 30 of different sizes, geometries, etc., with equidistant or variant spacing in-between the extension members 30 to accommodate the engine part to be rated.

In one embodiment, the grooves have a depth of about the same as the thickness of the extension sectioners 30a, allowing the extension sectioners 30a to stay flush with the plate surface. In one embodiment, the grooves have a depth of about $1/16$ to $1/4$".

In the embodiment as shown in FIG. 2, the grooves extend from the circumference (outside perimeter edge) of the plate, and radially inward toward and about $1/2$ to 1" away from the central hole 41. The length of the groove can be varied depending on the engine part (size) to be rated, and how well the extension members 30 are to be clamped in place in the grooves. As shown in FIG. 2, the extension members 30 can be the same or different. They can be of different lengths and bending at different angles. Some or all of the extension members 30 can have just one bend 30b of 90° to accommodate engine parts such as cylindrical pistons. Some of the extension members can have a plurality of bends 30b, allowing the section device 1 to be use to rate engine parts that may be smaller in size than the top or bottom plates.

In one embodiment as shown in FIG. 2, one of the extension members 30 has three bends 30b each at ninety-degree. One of the section dividers 30c has a downward length being perpendicular to the plates and an upward length being parallel to the downward length, and also perpendicular to the plates.

The top plate 10 and the bottom plate 20 are made from blanks of suitable materials such as metals, plastic materials, or alloys thereof, formed into shape via processes known in the art (e.g., forging, casting, or machining for metals and alloys; molding or extruding for plastics). In one embodiment, the extension members 30 are elongated solid (or tubular) members, made out of suitable materials such as metals, plastic materials, or alloys thereof. They can be of the same or different materials from the top plate 10 and the bottom plate 20. In one embodiment, the top and bottom plates are made from solid aluminum plates having a thickness of about 0.5". In another embodiment, the extension members 30 are made from steel bar stock. The gasket (not shown in Figures) can be made out of a compression material type, or a sheet of dense material, to prevent slippage between extension members 30 and the plate(s).

In the embodiment as illustrated, the top plate 10 and the bottom plate 20 are of equal size. However, they can be of the same or different sizes, as long as they can adequately hold the extension members 30 in place while still allowing the extension lengths 30a to be adjustably extended to accommodate the size of the engine part being rated.

In the embodiment as illustrated, the top plate 10 and the bottom plate 20 are circular. However, they can be of the same or different geometry, e.g., rectangular, square, circular, etc. to accommodate the shape and geometry of the engine part to be rated.

Besides varying the size and geometry of the plate(s) to accommodate the piston size, the length of the extension members 30 can also be varied to accommodate the piston size. Extension sectioners 30a can be longer than the length of the grooves, allowing the sectioners to "hang out" to accommodate accept a piston of a size much larger than the size of the bottom plate. A shorter extension sectioner 30a can also be used, riding in part way in the groove, for the section device to be used for rating a small piston.

In the embodiment as illustrated in FIG. 1, the extension members 30 are of equal size. However, they can be of different sizes (lengths), shapes and geometries as shown in FIG. 2 to accommodate the shape and geometry of the engine part to be rated.

Calibration of Engine Deposit Using the Sectioning Device:

In operation, the device operator simply loosens or disengages the fastener located on the sectioning device, allowing the top and bottom plates to slightly open apart. The loosely assembled device 1 is next placed on top of the engine part to be rated, e.g., a piston crown. The assembly in one embodiment can be positioned such that a particular (numbered—not shown in the Figures) groove is aligned with a pre-selected position on the piston, e.g., the centerline of the pin hole. The sectioners 30a can be first adjusted by pulling them outward or pushing them inward depending on the engine part, e.g., a piston, to be rated, such that the downward-bending section dividers 30c can close in around the piston head with little or minimal damages to the deposits. Lastly, the fastener is secured for the bends to engage with the piston head defining sections on the piston head, and the rating can proceed. Each section is defined by two adjacent downward-bending section dividers 30c.

In one embodiment, a device operator may want to use the section device without any of the extension members, i.e., placing the device (without the extension members) or the plate with the numbered grooves on the engine part to be rated. As the numbered grooves can be matched up with pre-determined positions on the piston head, e.g., groove 1 (not shown) is matched up with the centreline of the piston pin hole, the device operator can easily observe, track, and record the deposit growth on pre-designated sections on the engine part without destroying or with minimal loss of engine deposits.

As the sectioners length can be extended, the sectioning device can be used to section and rate engine parts of different sizes. For example, the same sectioning device can be used to "section" engine pistons parts of different sizes, e.g., a relatively small sized automobile engine piston to a larger sized tractor engine piston of three or four times the diameter size. In one embodiment, the same device can be used to rate a piston having a radius that is equal to the length of the sectioners, to a much larger piston having a radius twice the length of the sectioners by extending or pulling the sectioners further away from the grooves, e.g., pistons having diameters ranging from "6.5 to 11.5". Additionally, the same sectioning device can be used to rate engine deposits on different engine parts and different geometries, e.g., pistons, cylinders, and the like.

The section device has been described in an illustrative manner, and it is to be understood that the terminology which has been used is intended to be in the nature of words of description rather than of limitation. Many modifications and variations of the section device are possible in light of the above teachings. Various features, subcombinations, and combinations may be practiced with or without reference to other features. The invention is not to be limited except as defined by the appended claims.

All citations referred herein are expressly incorporated herein by reference.

The invention claimed is:

1. A device for use in dividing an engine part into sections for use in rating deposits on the engine part, the device comprising:
a first plate having a first opening formed through;
a second plate having a second opening formed through and aligning with the first opening in the first plate;
a plurality of grooves disposed on either a bottom surface of the first plate or a top surface of the second plate;
a plurality of extension members each having at least a bend defining an extension sectioner and an extension divider, the plurality of extension sectioners are disposed in the plurality of grooves and in-between the bottom surface of the first plate and the top surface of the second plate;
a fastener for fastening the top plate and the bottom plate through the aligned openings and securing the extension sectioners disposed in-between;
wherein, in deposit rating operation, the fastener is disengaged for the extension sectioners to be slidingly engaged in the grooves and the extension dividers to define separate sections on the engine part.

2. The device of claim 1, wherein the bend is at a ninety-degree angle with the extension sectioner, and wherein the extension divider is perpendicular to the first plate and the second plate.

3. The device of claim 1, wherein the extension members are of different lengths.

4. The device of claim 3, wherein the extension dividers define equal sections on the engine parts.

5. The device of claim 1, wherein the extension members are of different sizes and geometries.

6. The device of claim 1, wherein at least one of the extension members has at least two bends defining at least an extension divider, and wherein the extension divider defined by the bends is perpendicular to the first plate and the second plate.

7. The device of claim 1, wherein at least one extension divider is in engaging contact with the engine part.

8. The device of claim 1, further comprising a gasket disposed between the first plate and the second plate.

9. The device of claim 1, wherein the grooves are recesses machined onto the top surface of the second plate.

10. The device of claim 1, wherein the grooves are channels formed onto the bottom surface of the first plate.

11. The device of claim 1, wherein the first plate and the second plate are circular and the first plate is generally of the same size as the second plate.

12. The device of claim 11, wherein the grooves are disposed on the top surface of the second plate, and wherein the grooves are projected equidistantly and radially from the circumference of the second plate.

13. The device of claim 11, wherein the grooves are disposed on the bottom surface of the first plate, and wherein the grooves are projected equidistantly and radially from the circumference of the first plate.

14. The device of claim 1, wherein the plurality of extension sectioners are adjustably positioned in the grooves to rate engine parts of different sizes.

15. The device of claim 1, for rating pistons having diameters ranging from 6.5 to 11.5".

16. The device of claim 1, wherein the plurality of grooves are numbered for matching up with pre-determined positions on the engine part to be rated.

17. A device for use in dividing an engine part into sections for use in rating deposits on the engine part, the device comprising:
a first plate having a bottom surface and a side edge;
a second plate having a top surface and at least a side edge aligning with the side edge of the first plate;

a plurality of grooves disposed on either a bottom surface of the first plate or a top surface of the second plate;

a plurality of extension members each having at least a bend defining an extension sectioner and an extension divider, the plurality of extension sectioners are disposed in the plurality of grooves and in-between the bottom surface of the first plate and the top surface of the second plate;

a fastening clamp to fasten the top plate to the bottom plate at the aligned edges, and securing the extension sectioners disposed in-between;

wherein, in deposit rating operation, the fastening clamp is disengaged for the extension sectioners to be slidingly engaged in the grooves and the extension dividers to define separate sections on the engine part.

18. The device of claim 17, wherein the second plate is of the same size as the first plate.

19. A method for rating deposits on an engine part employing the sectioning device of claim 1, the method comprising the steps of:

disengaging the fastener to extend the sectioners around the engine part;

positioning the sectioning device onto the engine part to be rated;

adjusting the plurality of the extension sectioners so that the extension dividers define a plurality of separate sections on the engine part; and observing and recording deposits on the piston parts defined by the separate sections.

\* \* \* \* \*